United States Patent [19]
Boyd et al.

[11] Patent Number: 5,283,383
[45] Date of Patent: Feb. 1, 1994

[54] ANTITUMOR COMPOUND, COMPOSITIONS AND METHOD OF USE

[75] Inventors: Michael R. Boyd, Ijamsville; John H. Cardellina, II, Walkersville; Richard W. Fuller, Tracy's Landing; Kenneth M. Snader, Germantown, all of Md.; Jon Clardy, Ithaca, N.Y.

[73] Assignee: The United States of America as represented by the Department of Health and Human Services, Washington, D.C.

[21] Appl. No.: 835,637

[22] Filed: Feb. 18, 1992

[51] Int. Cl.$^5$ .................. C07C 21/02; C07C 21/14; A01N 29/02; A61K 31/035
[52] U.S. Cl. .................. 570/189; 514/744; 570/238
[58] Field of Search .................. 570/189, 238, 288; 514/744

[56] References Cited

U.S. PATENT DOCUMENTS 3,564,101  2/1971  Regan .................. 514/744
3,671,655  6/1972  Regan .................. 514/744

FOREIGN PATENT DOCUMENTS 112303   7/1982  Japan .................. 514/744
2144117  2/1985  United Kingdom .................. 570/189

OTHER PUBLICATIONS

Boyd, Michael R., Principles and Practice of Oncology Updates, ed. DeVita, Hellman & Rosenberg, vol. 3, #10, 1-12, 1989.
Burreson et al., Chemistry Letters 1111-1114, 1975.
Collins, Jerry M., *Cancer Chemotherapy: Principles and Practice* by Chabner and Collins, Chapter 2, J. B. Lippincott, Philadelphia, 1990.
Boyd et al., "Data Display and Analysis Strategies for the NCI Disease-Oriented *In Vitro* Antitumor Drug Screen", in *Anticancer Drug Discovery and Development*, eds Valerlote, F. A., Corbett, T. Baker, L.; Kluwer Academic Publishers, Amsterdam (in press 1990).
Monks et al., J. National Cancer Institute 83, No. 11, 757-766, 1991.
Boyd, Michael R. "The Future of Drug Development", in *Current Therapy in Oncology*; Section I. Introduction to Cancer Therapy; Chapter 2; ed Niederhuber; B. C. Decker, Inc., Philadelphia, (in press 1991).

Primary Examiner—Werren B. Lone
Attorney, Agent, or Firm—Leydig, Voit & Mayer

[57] ABSTRACT

The present invention relates to a new antitumor compound, a method for isolating same from a red alga, antitumor compositions containing same and methods of using same for treating patients with cancer. The compound of the present invention is 6(R)-bromo-3(S)-bromomethyl-7-methyl-2,3,7-trichloro-1-octene.

22 Claims, 4 Drawing Sheets

ANTITUMOR COMPOUND, COMPOSITIONS AND METHOD OF USE

BACKGROUND OF THE INVENTION

1. Field of the Invention

The present invention relates to a compound which exhibits antitumor activity, a method for isolating the compound from a red alga, and methods for using the compound. More specifically, the present invention relates to: isolation and identification of a new chemical compound, and of medically useful compositions containing the same. The compound of the present invention exhibits advantageous pharmacological, toxicological or antitumor properties, such as, for example, killing or inhibiting the growth of human tumors.

2. Description of Related Art

Since the mid-1970's the Rhodophyta (red algae) have been known to produce halogenated monoterpenes [Stallard, M. O., et al: Comp. Biochem. Physiol. B, 49: 25-35, 1974]. Although scores of acyclic, monocyclic and bicyclic halogenated monoterpenes have been identified [Sims, J. J., et al: In Marine Natural Products, Chemical and Biological Perspectives, (Scheuer, P. J., ed.), New York: Academic Press, 1978, pp. 297-378], this class of compounds has been confined to the genera Plocamium and Chondrococcus. The structure elucidation of these compounds has not been a simple task. The relatively volatile monoterpenes tend to decompose under electron-impact ionization mass spectrometry (EI-MS) conditions and acquisition of molecular weight and formula information has often been difficult. Correct placement of chlorine and bromine substituents has not proven to be straightforward, as NMR chemical shift arguments are clouded by the cumulative effects of multiple substituents on the $C_{10}$ skeleton.

The compound of the present invention is 6(R)-bromo-3(S)-bromomethyl-7-methyl-2,3,7-trichloro-1-octene. A compound proposed to have the same structure as the compound of the present invention was reported previously by Burreson et al., [Burreson, B. J., et al: Chemistry Lett., 1111-1114, 1975.] as an unresolved component in a mixture of monoterpenes from *Chondrococcus hornemannii;* however, the material was only partially characterized. Neither a proof of the structure, nor the absolute stereochemistry (there are two chiral centers, carbon atoms 3 and 6, and thus four possible diasteromers), nor a method of isolating the compound of the present invention in substantially pure form has previously been reported in the literature.

Other carbocyclic halomonoterpenes from Rhodophyta reportedly have shown general cytotoxicity in brine shrimp assays [Konig, G. M., et al: J. Nat. Prod. 53: 1615-1618, 1990] and in vitro inhibition of murine leukemia [Gonzales, A. G., et al: Planta Med. 44: 44-46, 1982] or other [Kusumi, T., et al: J. Org. Chem. 52: 4597-4600, 1987] cell lines. However, the novel profiles of selective antitumor activity of the compound of the present invention that can be demonstrated in the U.S. National Cancer Institute's new disease-oriented primary screen, which predicts antitumor activity against human solid tumors, has not previously been reported for any halomonoterpene in the literature. Neither the specific compound of the invention nor pharmaceutical compositions of the compound nor methods of using the compound or compositions thereof for treatment of cancer have been heretofore described.

SUMMARY OF THE INVENTION

The present invention is directed to a new compound, in substantially pure form and having the structure:

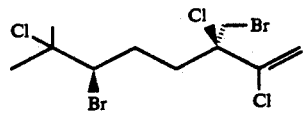

The present invention also is directed to a method of isolating and purifying the compound of the present invention from a red alga.

Another aspect of the present invention is directed to antitumor compositions which comprise an antitumor effective amount of the compound of the present invention and a pharmaceutically acceptable carrier.

Any of the above antitumor compositions can further include an antitumor effective amount of one or more other known antitumor agent.

The present invention also is directed to a method of treating cancer which comprises administering to a patient in need thereof, an antitumor effective amount of the compound of the present invention.

The method of the present invention also comprises coadministering an antitumor effective amount of one or more other known antitumor agent, together with the compound of the present invention.

Further scope of the applicability of the present invention is apparent from the detailed descriptions and drawings provided below. However, it should be understood that the detailed descriptions and specific examples, while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention is illustrated further in the accompanying drawings wherein:

FIG. 2 demonstrates the broad anticancer efficacy of the compound.

DETAILED DESCRIPTION OF THE INVENTION

Figure 1:
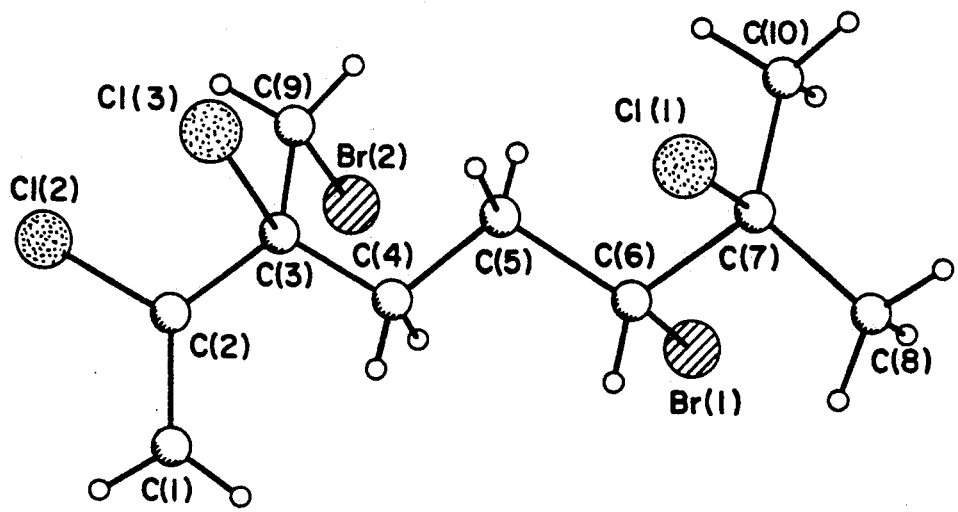
FIG. 1 illustrates the x-ray crystal structure and absolute stereochemistry of the compound of the present invention.

The present invention specifically relates to a compound [6(R)-bromo-3(S)-bromomethyl-7-methyl-2,3,7-trichloro-1-octene] which has novel antitumor activity, methods of obtaining same from red alga, compositions containing same, and methods of using the compound or compositions of same for treating cancer.

A variety of methods can be used for isolation of the compound of the present invention. Most generally the compound is extracted from a red alga using an organic solvent. The compound can be further purified by chromatography (column or HPLC) and/or by recrystallization. A fresh red alga can be used as the source, but generally the alga is frozen immediately after harvesting. This alga is then used directly or freeze-dried before the extraction is done. Preferably the red alga is *Portieria hornemannii*, most preferably *Portieria hornemannii* collected near Chanaryan, Batan Island, in the Philippines, see Example 1. A preferred general method of isolating the compound of the invention is:

a) obtaining a fresh or frozen sample of said red alga, b) extracting said compound from said sample with an organic solvent which dissolves said compound, to form an extract, c) partitioning said extract between a nonpolar organic solvent and an aqueous solvent, to form a partitioned nonpolar organic extract, d) chromatographing said partitioned nonpolar organic extract on an adsorption, partition or size exclusion matrix to form fractions, e) isolating said compound from said fraction containing it.

In step b) the organic solvent which dissolves the compound is generally a mixture of a nonpolar organic solvent and a polar organic solvent; the nonpolar organic solvents include $CH_2Cl_2$, $CHCl_3$, toluene and hexane; the polar organic solvents include MeOH, EtOH, isopropyl alcohol and acetone. In step c) the organic nonpolar solvents include $CH_2Cl_2$, hexane, $CCl_4$, $CHCl_3$, and ethyl acetate; and typical aqueous solvents are mixtures of water and methanol. Solvent mixtures that can be used in this partitioning step are: a) $CH_2Cl_2$ vs 19:1 $H_2O$-MeOH, b) hexane vs 9:1 MeOH-$H_2O$, c) $CCl_4$ vs 8:2 MeOH-$H_2O$, d) $CHCl_3$ vs 7:3 MeOH-$H_2O$, and e) EtOAc vs $H_2O$. In step d) the chromatography is column chromatography and the chromatographic matrix can be the adsorption type, or the partition type or the size exclusion type, or a combination of any of these types. Sephadex LH-20 combines all three of these types, and is characterized by mild treatment and good recoveries. Sephadex LH-20 is the most preferred chromatographic matrix material. The isolation of step e) is carried out by either simply evaporating the solvent or by recrystallization.

A typical procedure is as follows. A sample of the frozen red alga was lyophilized and extracted with $CH_2Cl_2$-MeOH (1:1), followed by a MeOH rinse. The crude organic extract was partitioned between $CH_2Cl_2$ and $H_2O$-MeOH (19:1). The dichloromethane phase was reduced, in vacuo, and permeated through Sephadex LH-20 (column 2.5×190 cm) with $CH_2Cl_2$-MeOH (1:1) at 1-2 ml/min. Approximately three column volumes were used to elute the extracts. Fractions were monitored by and separated on the basis of UV absorption at 254 nm; fraction volumes thus vary. The seventh fraction was known to contain the compound of the invention because it was cytotoxic in the HIV screen and because the compound crystallized on evaporation of the solvent. The seventh fraction was crystallized from MeOH to give the compound of the present invention in substantially pure form.

The definitive proofs of the structure of the compound of the present invention can be obtained by a combination of methods including primary spectral analyses (e.g., high-resolution NMR and mass spectrometry, infrared and UV spectroscopy), comparisons of spectral and physicochemical properties with related literature precedents, and by x-ray crystallographic analysis.

Figure 3:
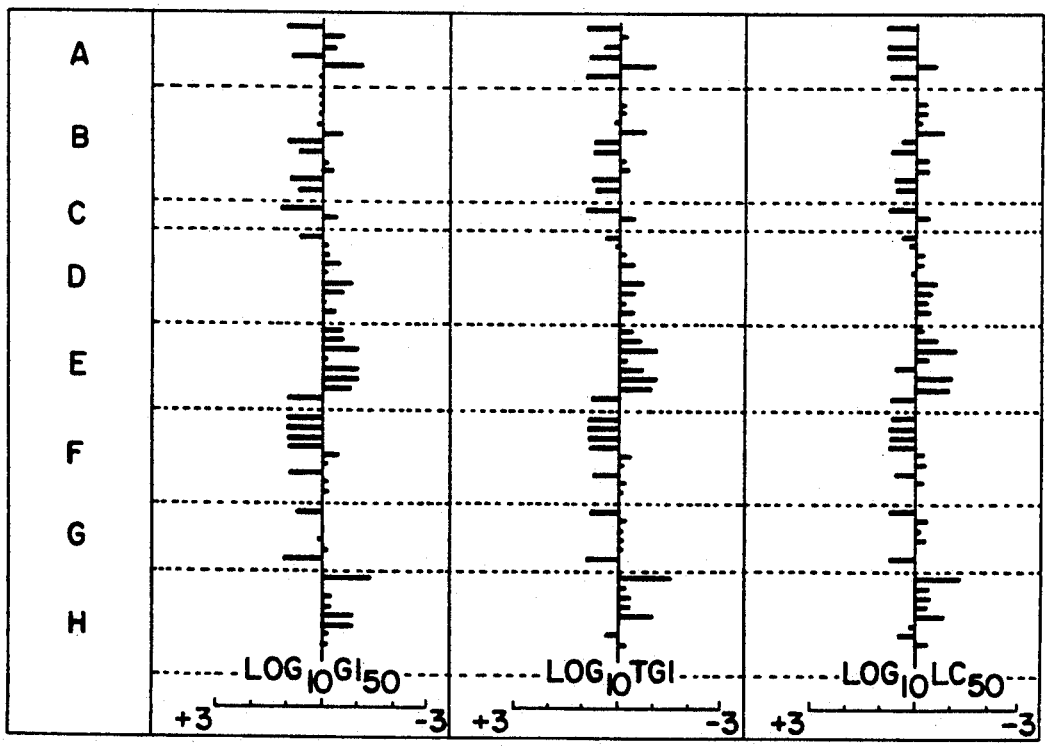
FIG. 3 illustrates mean graphs derived from the doseresponse curves of FIG. 2; the letters of the subpanels shown in the mean graphs correspond directly to the respective identifiers for the subpanel graphs of FIG. 2. The centerlines about which the $GI_{50}$, TGI, and $LC_{50}$ mean graphs are constructed represent negative $log_{10}$ molar concentrations of 1 of 5.59, 5.13 and 4.70, respectively. These three values are the average values over the 60 cell lines. These response parameters are defined in Example 3. Bars projecting to the right of the centerlines represent cell lines proportionately more sensitive, whereas bars projecting to the left of the centerlines are proportionately less sensitive.
Figure 2A:
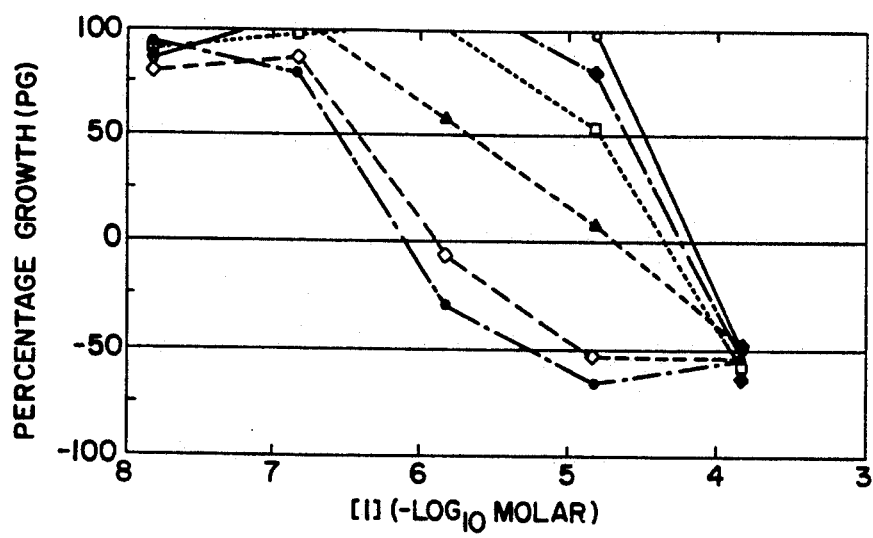
FIG. 2 illustrates dose-response curves from the testing of the compound of the present invention against the cell line subpanels comprising the NCI's human tumor, disease-oriented in vitro screen. Individual cell line identifiers are omitted for clarity. Graph A is from the leukemia/lymphoma subpanel, graph B the non small-cell lung cancer subpanel, graph C the small-cell lung cancer subpanel, graph D the colon cancer subpanel, graph E the brain tumor subpanel, graph F the melanoma subpanel, graph G the ovarian cancer subpanel, graph H the renal cancer subpanel; graph I shows a composite of all the respective subpanels together. Percentage Growth (PG) is defined in Example 3.
Figure 2B:
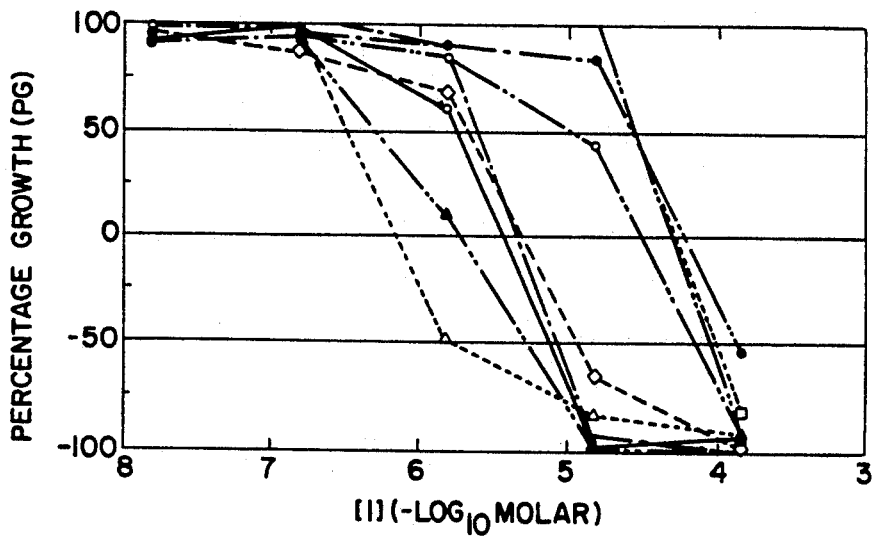
Figure 2C:
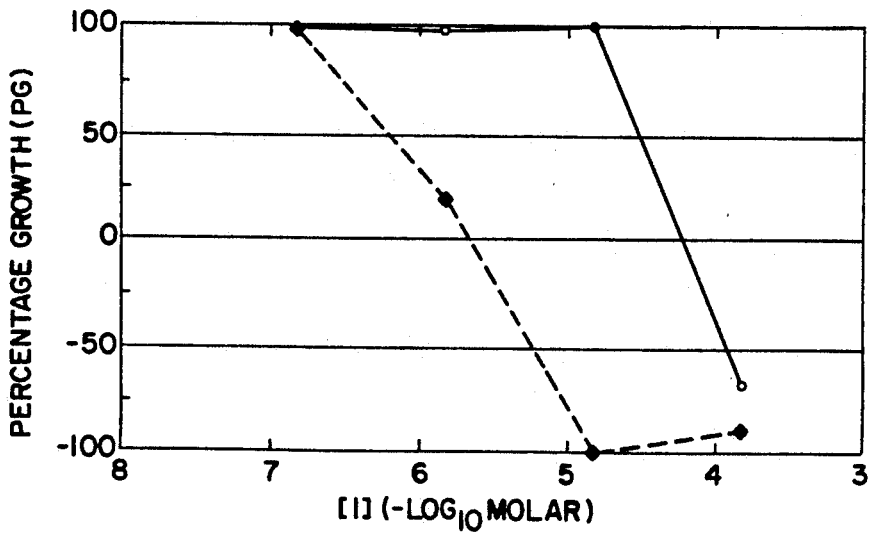
Figure 2D:
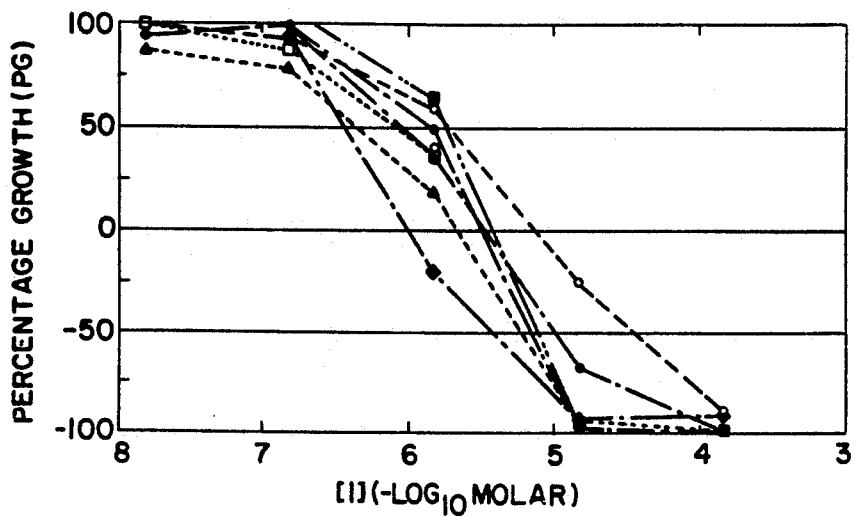
Figure 2E:
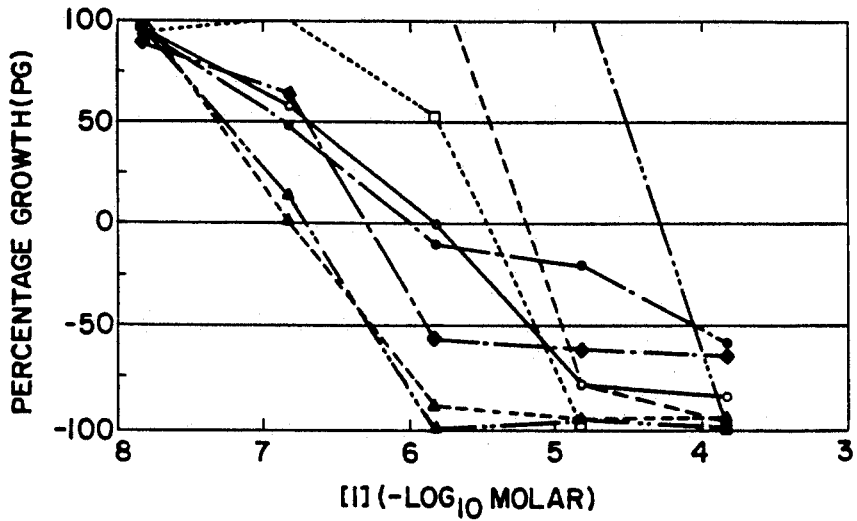
Figure 2F:
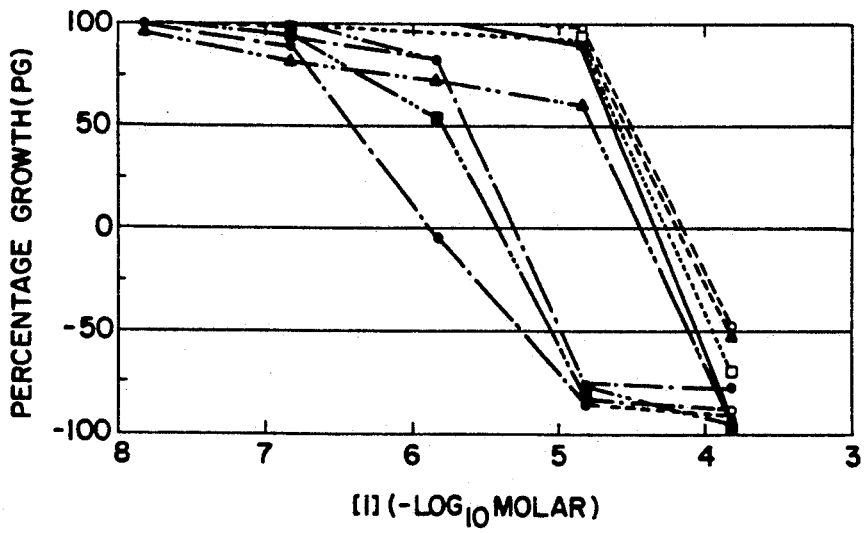
Figure 2G:
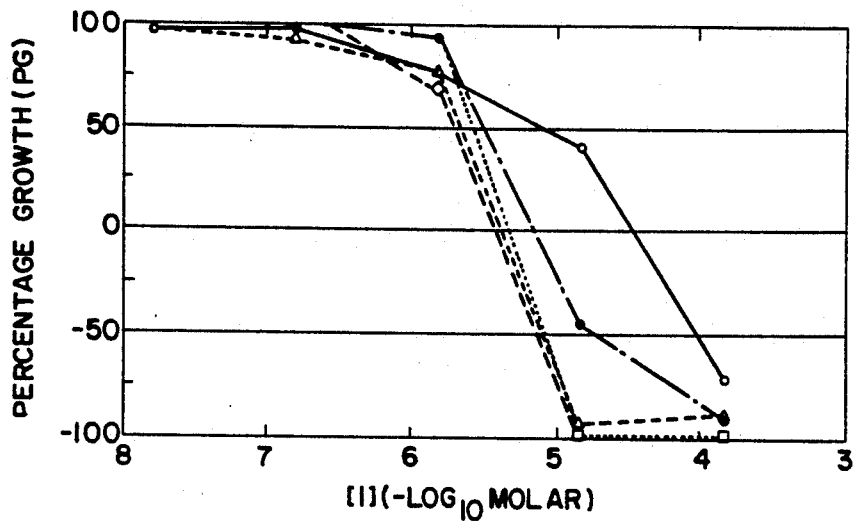
Figure 2H:
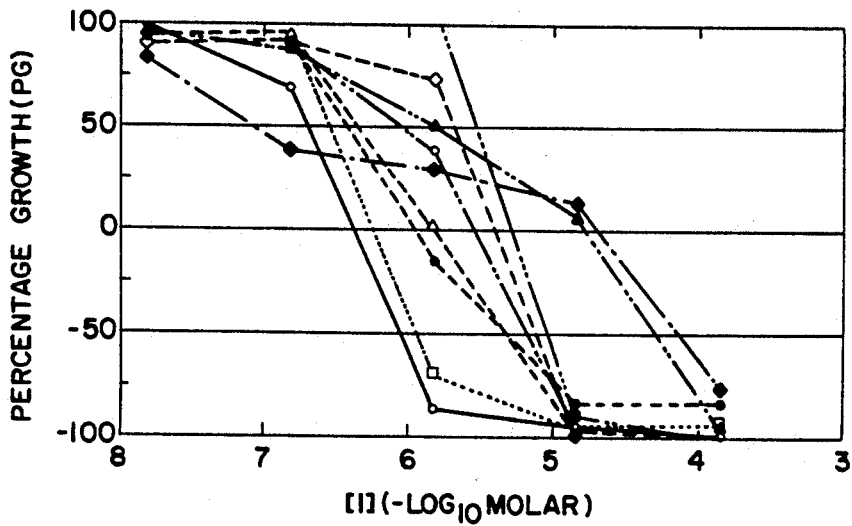
Figure 2I:
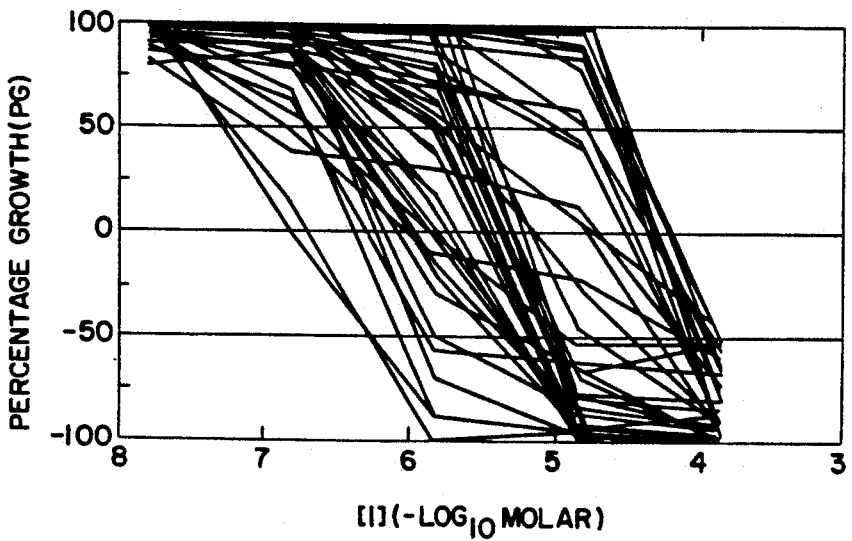

The novel antitumor activity of the compound of the present invention can be demonstrated in the U.S. National Cancer Institute's new human tumor, disease-oriented screen [Boyd, M. R.: In CANCER: Principles and Practice of Oncology. Update Series. (DeVita, V. T. Jr., Hellman, S., and Rosenberg, S. A., eds.), Philadelphia: Lippincott, 1989, pp. 1-12; Boyd, M. R.: In Current Therapy in Oncology (Niederhuber, J. E., ed.) Philadelphia: B. C. Decker, Inc., 1991, in press, both of which references are hereby incorporated by reference in their entirety], which accurately predicts antitumor activity of chemical compounds against human cancers. This screen measures the ability of the compound to selectively kill or inhibit the growth of diverse human cancers. More specifically, using this screen, it can be shown that the compound of the present invention is highly active against certain types of human solid tumors (e.g., brain cancer, renal cancer and colon cancer) which are very resistant or completely resistant to existing antitumor drugs; and, it can be shown that the compound is also active against other human solid tumors and leukemia cancer cells. By these observations, and with other detailed analyses of the characteristic tumor cellular response profile produced by the compound of the present invention in the above screen (see example 3), it can be shown that the same compound is a highly novel antitumor agent with an unprecedented structure-activity relationship for treatment of human solid tumors. It is unusual for a compound to be more active against human solid tumor cell lines than human leukemia cell lines. The compound of the invention is thus shown to be a new and broadly efficacious anticancer agent. The results shown in Example 3 and in FIGS. 2 and 3 show that the compound is efficacious against human leukemias, lymphomas and solid tumors. Solid tumors include lung cancer, colon cancer, brain cancer, melanoma, ovarian cancer, renal cancer, head and neck cancer, testicular cancer, germ-line cancers, endocrine tumors, uterine cancer, breast cancer, sarcomas, gastric cancer, hepatic cancer, esophageal cancer and pancreatic cancer.

Compositions of the present invention comprise as the active ingredient, the compound of the present invention and a pharmaceutically acceptable carrier. Suitable carriers for use in the present invention include, but are not limited to, injectable or orally or rectally administrable oils, lipid emulsions, aqueous solutions or suspensions, or, in the case of orally or rectally administrable tablets or capsules, a pharmacologically inert excipient.

The compound and compositions of the present invention can be shown to kill or inhibit the growth of human cancer, both leukemic and solid tumor cancers; more particularly solid tumors, most particularly tumors of the brain, kidney and colon.

The present invention further relates to a method of preventing or treating cancer comprising administering to a patient an "antitumor effective amount" of a composition of the present invention. The composition can be administered, for example, orally, subcutaneously or intravenously. The composition can be present as a solution suitable, for example, for intravenous injection or infusion. The composition can also be present in unit dosage form, such as, for example, a tablet or capsule. The "antitumor effective amount" is the dose necessary to achieve an "effective level" in the individual patient Since the "effective level" is used as the preferred endpoint for dosing, the actual dose and schedule may vary, depending upon interindividual differences in pharmacokinetics, drug distribution and metabolism. The "effective level" may be defined, for example, as the blood or tissue level desired in the patient that corresponds to a concentration of the compound of the present invention which kills or inhibits the growth of human tumors in an assay which can predict for clinical antitumor activity of chemical compounds. The "effective level" for compounds of the present invention also may vary when the compositions of the present invention are used in combination with other known antitumor compounds or combinations thereof. One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with clinical chemistry indicators) analysis of appropriate patient samples (e.g., blood and/or tissues), or by direct or indirect observations of the shrinkage or inhibition of growth of the individual patient's tumor. There are many references in the art that teach how one works out the protocols of administering anticancer agents to patients, see for example "Cancer Chemotherapy: Principles and Practice" ed. Chabner and Collins, J. B. Lippincott, 1990, especially chapter 2, by J. B. Collins, which is hereby incorporated by reference in its entirety.

The method of treating cancer using the compound of the invention can be made more effective by administering other anticancer compounds along with the compound of the invention. These other anticancer compounds would include all of the known anticancer compounds approved for marketing in the United States and those that will become approved in the future. See, for example Table 1 and Table 2 of Boyd "The Future of Drug Development" (In Press in J. E. Niederhuber, Ed., Current Therapy in Oncology; Section I. Introduction to Cancer Therapy; Chapter 2., B. C., Decker, Inc., Philadelphia, 1991, which is hereby incorporated by reference in its entirety). More particularly, these other anticancer compounds would include doxorubicin, bleomycin, vincristine, vinblastine, VP-16, VW-26, cisplatin, procarbozine and taxol for solid tumors in general; alkylating agents, such as BCNU, CCNU, methyl-CCNU and DTIC for brain or kidney cancers; and, antimetabolites such as 5-FU and methotrexate for colon cancer.

EXAMPLES

The following non-limiting EXAMPLES are provided to aid in the understanding of the present invention. It is understood in turn that modifications can be made in the procedures set forth without departing substantially from the true spirit and scope of the invention.

EXAMPLE 1: Isolation of the Compound of the Present Invention from Extracts of the Red Alga Portieria hornemannii

*Portieria hornemannii* (Lyngbye) P. C. Silva (=*Chondrococcus hornemannii*) was collected by NCI contractor Ernani G. Menez near Chanaryan, Batan Island, in the Philippines in April, 1986. A voucher specimen is on deposit at the Smithsonian Institution, recorded with the collector's number Q671573. The alga was frozen immediately after collection, at −20° C. A 1 kg sample of the frozen material was lyophilized and extracted with $CH_2Cl_2$-MeOH (1:1), followed by a MeOH rinse (once with each solvent, the quantity used was sufficient to cover the sample). The two solvents were combined, evaporated at less than 40° C. to form a crude organic extract (2.5g). This was partitioned between $CH_2Cl_2$ (100 mL) and $H_2O$-MeOH (19:1, 100 mL). The dichloromethane phase was reduced, in vacuo, and permeated through Sephadex LH-20 (column 2.5×190 cm) with $CH_2Cl_2$-MeOH (1:1) at 1-2 ml/min. Approximately three column volumes were used to eluate the extracts. Fractions were monitored by and separated on the basis of UV absorption at 254 nm; each fraction represents a peak in the UV absorbance, thus fraction volumes vary. The seventh fraction was known to contain the compound of the invention because it was cytotoxic and because the compound crystallized on evaporation of the solvent. The seventh fraction was crystallized from MeOH to give 55 mg of the compound of the present invention in substantially pure form.

EXAMPLE 2: Structure Proof of the Compound of the Present Invention

Preliminary $^1H$ and $^{13}C$ nmr analyses suggested a monoterpene. While EI-MS failed to provide a discernible molecular ion or M-HX fragment ion, chemical ionization-mass spectroscopy (CI-MS) did reveal a weak pseudomolecular ion cluster beginning at m/z 416 ($M+NH_4+$), which corresponded to the molecular formula $C_{10}H_{15}Br_2Cl_3$; this was confirmed by high resolution EIMS.

An earlier report [Burreson, B. J., et al: Chemistry Lett. 1111-1114, 1975] showed a compound proposed to have the same structure as the compound of the present invention; however, their material was an unresolved component in a mixture of monoterpenes from *Chondrococcus hornemannii;* moreover, the material was only partially characterized. The exact stereochemical structure of the Burreson et al. compound was not disclosed in this reference, nor was the compound ever isolated in pure form, nor was any method taught that might be used to isolate the compound, nor was any method taught that could be used to synthesize the compound. Thus it is not known whether the compound of Burreson is the same as that of the present invention (there ar four possible diastereomers with the structure of the Burreson et al. compound); it is clear, however, that Burreson et al. never put the compound of this invention (nor the one he partially characterized) into the hands of the public.

For proof of the structure of the compound of the present invention, in addition to our x-ray analysis, we used $^1H$-$^1H$ COSY, HMQC and HMBC experiments to assign definitively all the resonances in the $^1H$ and $^{13}C$ nmr spectra of 1, see Table 1.

TABLE 1

$^1H$ and $^{13}C$ NMR Assignments, Compound 1

| Carbon/ Hydrogen # | $^{13}C^b$ | $^1H^c$ |
|---|---|---|
| 1 | 118.5 | 5.61 (d,2.4) |
|   | 5.84 | (d,2.4) |
| 2 | 139.7 | — |
| 3 | 73.8 | — |
| 4 | 37.8 | 2.53 (ddd,13.2,10.2,1.9) |
|   |   | 2.14 (t, 10.2) |
| 5 | 30.1 | 2.48 (ddd,13.2,11.5,1.5) |
|   |   | 1.97 (dddd,11.5,11.2,10.2,1.9) |
| 6 | 64.6 | 4.02 (dd,11.2,1.5) |
| 7 | 71.6 | — |
| 8 | 27.1 | 1.66 (s) |
| 9 | 38.6 | 3.83 (d,10.7) |
|   |   | 3.77 (d,10.7) |
| 10 | 33.1 | 1.77 (s) |

$^a$recorded in $CDCl_3$ on a Varian VXR-500 spectrometer
$^b$125 MHZ, δ
$^c$500 MHZ, δ (multiplicity, J in Hz)

Other spectral and physicochemical data for the compound of the present invention are as follows: Mp 49°-50°;$[\alpha]_D$ +206° (c 1.08, $CH_2Cl_2$); CI-MS ($NH_3$): m/z 416/418/420/422/424 ($MNH_4+$, 0.3/1.0/1.0/0.5/0.1), 336/338/340/342 (1.8/3.3/2.2/0.6), 300/302/304 (4.3/6.9/3.4), 247/249 (17/22), 203/205 (19/13), 167/169 (27/24), 96/66, 52 (100); HREIMS m/z 401.8583 (calc'd for $C_{10}H_{15}{}^{35}Cl{}^{37}Cl_2{}^{79}Br_2$-401.8619), 399.8637 (calc'd for $C_{10}H_{15}{}^{35}Cl{}^{37}Cl_2{}^{79}Br_2$ -399.8679).

The final definitive proof of the structure of the compound of the present invention was from single-crystal x-ray diffraction analysis. The compound was crystallized from n-pentane by slow evaporation at −25° C. and appeared as clear thin plates. A specimen with approximate dimensions 0.1×0.15×0.2 mm was selected for analysis. Preliminary x-ray photographs displayed orthorhombic symmetry. Accurate lattice constants of a=6.115(4), b=12.456(6), c=19.188(10)Å were determined from 30 diffractometer measured 2θ-values. Systematic extinctions, optical activity, and crystal density were consistent with space group $P2_12_12_1$ with one molecule of composition $C_{10}H_{15}Br_2Cl_3$ forming the asymmetric unit. Additional crystallographic parameters were V=1461.6(14)Å$^3$, μ(MoKα) 6.02 mm$^{-1}$, and $D_c$=1.824 g cm$^{-3}$ for Z=4. Intensity data were collected on a Nicolet (Siemens) $P2_1$ diffractometer with MoKα radiation (0.71073 Å) and a 2θ:θ scan technique. A total of 1157 Friedel unique data were collected, of which 686 (59%) with $|F_o| \geq 4\sigma(|F_o|)$ were considered observed after correction for Lorentz, polarization and background effects. The structure was solved by direct methods and refined by full-matrix, least-squares techniques [Sheldrick, G. M. SHELXTL Crystallographic System (Siemens Instrument Division: Madison, Wis.), 1986]. The final refinements with anisotropic thermal parameters for all nonhydrogen atoms, riding isotropic hydrogens, and anomalous scattering corrections for bromine and chlorine converged smoothly to a final discrepancy index of 7.81% for the enantiomer shown (wR 6.72%). The other enantiomer converged to the significantly higher value of 8.51%. The absolute configuration also was ascertained by the eta-test. The enantiomer shown refined to eta +1.1(2) [Sheldrick, G. M.: SHELXTL Crystallographic System (Siemens Instrument Division: Madison, Wis.), 1986]. A computer-generated perspective model of the final model is given in FIG. 1; archival crystallographic data have been deposited with the Cambridge Crystallographic Data Centre, Cambridge, U.K.

EXAMPLE 3: Antitumor Activity of the Compound of the Present Invention

The pure compound of the present invention was tested in the NCI's human tumor, disease-oriented in vitro screen [Boyd, M. R.: In CANCER: Principles and Practice of Oncology Update. (DeVita, V. T. Jr., Hellman, S., and Rosenberg, S. A., eds.), Philadelphia: Lippincott, 1989, pp. 1–12] as described elsewhere [Boyd, M. R.: In CANCER: Principles and Practice of Oncology Update. (DeVita, V. T. Jr., Hellman, S, and Rosenberg, SA, eds.), Philadelphia: Lippincott, 1989, pp. 1–12; Boyd, M. R., et al.: In Antitumor Drug Discovery and Development (Valeriote, F. A., Corbett, T., Baker, L. eds.), Amsterdam: Kluwer Academic Publishers, 1991, in press; Monks, A., et al.: J. Natl. Cancer Inst. 83: 757–766, 1991]. Briefly, stock solutions of the compounds were prepared initially in dimethylsulfoxide at 400x the desired final highest test concentration and stored at −70° until use. The desired final highest test concentration is the highest achievable in the test medium and is between $10^{-3}$ and $10^{-4}$ molar. At the time of screening, an aliquot of the thawed stock was diluted with complete medium containing 50μg/ml gentamycin to give a concentration of 2x the desired final highest test concentration. An additional four, 10-fold serial dilutions were then made to provide a total of five concentrations, spanning a 4-$\log_{10}$ concentration range. One hundred μl aliquots of these intermediate dilutions were immediately added to the appropriate microtitre wells, each already containing the appropriate numbers and types of cells in 100μl of culture medium, resulting in the desired five final concentrations.

The 60 cell lines used, and the respective inoculation densities, were the same as described elsewhere [Monks, A., et al.: J. Natl. Cancer Inst. 83: 757–766, 1991; which is hereby incorporated by reference in its entirety]. Following the compound additions, the plates were incubated for 48 hr at 37° C. under a 5% $CO_2$/air atmosphere and 100% humidity. Then, adherent cells (all lines except the leukemias) were fixed in situ by gentle addition of cold trichloroacetic acid (50 microliters of 50% w/v) and incubated for 60 min. at 4° C. Supernatants were discarded, the plates washed x5 with deionized water and air dried. Sulforhodamine B solution (SRB; 100μl at 0.4% w/v in 1% acetic acid, see Monks et al., supra, for more details) was added to each plate, followed by further incubation for 10 min. at room temperature. Excess unbound dye was then removed by washing x5 with 1% acetic acid, followed by air drying. The bound stain in each well was solubilized by addition of 100 microliters of 10 millimolar unbuffered Tris base; this was followed by determination of optical densities (515nm) on an automated plate reader. For suspension cell cultures (the leukemias), the method was the same except that at the end of the drug incubation period the settled cells were fixed in situ to the bottoms of the microtitre wells by gentle addition of 50 μl of 80% trichloracetic acid.

Appropriate control wells were included in the test plate format [Monks, A., et al.: J. Natl. Cancer Inst. 83: 757–766, 1991] to allow subtraction of background optical densities, drug-blank corrections and determination of cell densities at time 0 (the time at which compounds are added). A single test of the compound performed in the above manner required the equivalent of ten 96-well microtitre plates of the compound of the present invention.

Data calculations employed the three experimental measurements: control optical densities ((C) in which cells are present but no test compound), test optical densities ((T) in which both the cells and test compound are present) and optical densities at time zero (To(. If $T \geq To$, then the calculation for percentage growth (PG) was $100 \times [(T-To)/(C-To)]$. If $T \leq To$, the PG calculation was $100 \times [(T-To)/To)]$. For each cell line a five-point dose-response curve was created, and the three response parameters, $GI_{50}$, TGI and $LC_{50}$, were calculated for each cell line. $GI_{50}$ stands for growth inhibiting concentration for a 50% decrease in net cell growth. The $GI_{50}$ was calculated for each line where $PG = 100 \times [(T-To)/(C-To)] = 50$; this value corresponds to the drug concentration causing a 50% decrease in net cell growth during the drug incubation. The drug concentration resulting in total growth inhibition, or TGI, is calculated from $T = To$; this corresponds to the drug concentration yielding an amount of cellular protein at the end of the incubation that is the same as at the beginning of the incubation (PG0). Finally, the $LC_{50}$ parameter (Lethal concentration) is calculated from $PG = 100 \times [(T-To)/To] = -50$. The $LC_{50}$ corresponds to the drug concentration causing a net 50% reduction in the measured protein at the end of the incubation compared with that at the beginning (i.e. a net loss of cells). Having all parameters thus calculated for each compound for each cell line, the construction of the respective mean graphs and other graphical displays, data calculations, and analyses were performed as described elsewhere [Boyd, M. R., et al.: In Antitumor Drug Discovery and Development, Valeriote, F. A., Corbett, T., Bakers, L., eds., Amsterdam: Kluwer Academic Publishers, 1991, in press, incorporated by reference in its entirety; Monks, A., et al.: J. Natl. Cancer Inst. 83: 757–766, 1991] by computer.

The data shown in FIGS. 2 and 3 are representative of quadruplicate tests of the compound of the present invention. The negative $\log_{10}$ $GI_{50}$, TGI and $LC_{50}$ values, respectively, calculated for each individual cancer cell line in this experiment and used to construct the corresponding mean graphs of FIG. 3 are listed as follows by subpanel, with the individual cell line names therein listed in the same order as their data appear top-to-bottom on the mean graphs of FIG. 3.

A1(leukemia/lymphoma subpanel): CCRF-CEM (4.54, 4.16. 3.82), HL-60 TB (6.12, 5.36, 4.68), K-562 (5.92, 4.66, 3.85), MOLT-4 (4.68, 4.23, 3.85), RPMI-8226 (6.68, 6.15, 5.21), SR (5.47, 4.14, 3.89; B1(non small-cell lung cancer subpanel): A549/ATCC (5.54, 5.17, 4.72), EKVX (5.52, 5.24, 4.96), HOP-18 (5.49, 5.21, 4.92), HOP-62 (5.38, 5.05, 4.77), HOP-92 (6.14, 5.82, 5.44), NCI-H226 (4.62, 4.41, 4.21), NCI-H23 (4.85, 4.38, 4.00), NCI-H322M (5.68, 5.34, 5.02), NCI-H460 (5.82, 5.44, 5.08), NCI-H22 (4.62, 4.34, 4.06), LXFL-529L (4.85, 4.47, 4.12); C1(small-cell lung cancer subpanel): DMS 114 (4.3S, 4.12, 3.89), DMS 273 (5.96, 5.49, 5.10); D1(colon cancer subpanel): COLO 205 (4.92, 4.70, 4.24), DLD-1 (5.74, 5.00, 4.46), HCC-2998 (5.77, 5.35, 5.00), HCT-116 (6.04, 5.49, 4.92), HCT-15 (5.66, 5.15, 4.62), HT29 (6.44, 5.85, 5.28), KM12 (6.17, 5.59, 5.116), KM20L2 5.64, 5.33, 5.00), SW-620 (5.96, 5.52, 5.09); E1(brain tumor subpanel): SF-268 (6.16, 5.54, 4.96), SF-295 (6.17, 5.70, 5.30), SF-539 (6.57, 6.19, 5.77), SNB-19 (5.70, 5.37, 5.04), SNB-75 (6.59, 5.80, 4.10), SNB-78 (6.60, 6.19, 5.70), U251 (6.40, 6.00, 5.64), XF498 (4.59, 4.30, 4.02); F1(melanoma subpanel): LOX IMVI (4.57, 4.24, 4.00), MALME-3M (4.57, 4.20, 3.89), M14 (4.57, 4.21, 3.92), M19-MEL (4.62, 4.24, 3.92), SK-MEL-2 (6.01, 5.49, 4.89), SK-MEL-28 (5.64, 5.32, 5.01), SK-MEL-5 (4.66, 4.38, 4.09), UACC-257 (5.68, 5.31, 4.89), UACC-62 (5.66, 5.17, 4.70); G1(ovarian cancer subpanel): IGROV1 (4.82, 4.37, 3.96), OVCAR-3 (5.59, 5.33, 5.07), VCAR-4 (5.57, 5.24, 4.85), OVCAR-5 (5.49, 5.24, 5.00), OVCAR-8 (5.72, 5.21, 4.66), SK-OV-3 (4.48, 4.21, 3.96); H1(renal cancer subpanel): 786-0 (7.02, 6.66, 6.00), A498 (5.62, 5.34, 5.07), ACHN (5.85, 5.49, 5.15), CAKI-1 (5.80, 5.47, 5.05), RXF-393 (6.48, 6.06, 5.51), RXF-631 (6.47, 5.11, 4.52), SN12C (5.74, 4.77, 4.24), TK-10 (5.6S, 5.37, 5.08), UO-31 (5.57, 5.19, 4.82).

There was an unusually broad range of differential sensitivities among the various types of human tumors to the antitumor effects of the compound of the present invention (FIGS. 2, 3); for example, compared to the less sensitive melanoma and leukemia lines, several of the more sensitive brain, renal and colon tumor cell lines were as much as a 1000-fold or more sensitive at the $GI_{50}$ response level. The compound of the present invention thus has a highly novel antitumor activity profile in the NCI screen; it has preferential antitumor activity toward human solid tumors; available antitumor drugs do not show such activity in this screen and likewise are generally ineffective in the treatment or cure of such tumors; available antitumor drugs usually are most effective for treatment or cure of leukemias and lymphomas [Boyd, M. R.: In CANCER: Principles and Practice of Oncology Update. (DeVita, V. T. Jr., Hellman, S., and Rosenberg, S. A., eds.), Philadelphia: Lippincott, 1989, pp. 1–12; Boyd, M. R.: In Current Therapy in Oncology. (Niederhuber, J. E., ed.), Philadelphia: B. C. Decker, Inc., 1991, in press]. The compound of the present invention further appears to act by an antitumor mechanism different than known conventional antitumor drugs; for example, it does not appear to act merely as an electrophile (alkylating agent); consistent with this view were results of computerized pattern-recognition studies, using the COMPARE algorithms [Paull, K. D., et al.: J. Natl. Cancer Inst. 81; 1088–1092, 1989] which showed no resemblance of the mean graph profiles of the compound of the present invention (FIG. 3) to known alkylating agents; nor does the screening profile or "fingerprint" of the compound match by COMPARE with any other known conventional antitumor drug currently available.

EXAMPLE 4. Pharmaceutical Compositions

The compound of the present invention or antitumor derivatives thereof may be made into pharmaceutical compositions by combination with appropriate, pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration In pharmaceutical dosage forms, the compound employed in the present invention may be used alone or in appropriate association, as well as in combination with other pharmaceutically active compounds, including other antitumor compounds. These other antitumor compounds are described supra.

The following methods and excipients are merely exemplary and are in no way limiting. In the case of oral preparations, the compound of the present invention may be used alone, or in combination with other antitumor agents, together with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compound of the present invention may alone, or in combination with other antitumor agents, be formulated into preparations for injections by dissolving, suspending or emulsifying in an aqueous or nonaqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compound of the present invention, alone or in combination with other antitumor compounds, can be made into aerosol formulations to be administered via inhalation. These aerosol formulations can be placed into pressurized acceptable propellants such as dichlorodifluoromethane, propane, nitrogen and the like.

Furthermore, the compound of the present invention, alone or in combination with other antitumor agents, may be made into suppositories by mixing with a variety of bases such as emulsifying bases or water-soluble bases. The suppository formulations can be administered rectally; the suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, e.g., teaspoonful, tablespoonful, tablet or suppository contains a predetermined amount of the composition containing the compound of the present invention, alone or in combination with other antitumor agents; similarly, unit dosage forms for injection or intravenous administration may comprise a composition as a solution in sterile water, normal saline or other pharmaceutically acceptably carrier.

The term "unit dosage form" as used herein refers to physically discrete units suitable as unitary dosages for human and animal subjects, each unit containing a predetermined quantity of the compound of the present invention, alone or in combination with other antitumor agents, calculated in an amount sufficient to produce the desired effect in association with a pharmaceutically acceptable, diluent, carrier or vehicle. The specifications for the novel unit dosage forms of the present invention depend on the particular effect to be achieved, and the particular pharmacodynamics associated with the compound in the individual host.

The pharmaceutically acceptable excipients, for example vehicles, adjuvants, carriers or diluents, are readily available to the public.

One skilled in the art can easily determine the appropriate method of administration for the exact formulation of the composition being used. Any necessary adjustments in dose can be made readily to meet the nature or severity of the cancer, and the individual patient's overall physical health, and adjusted accordingly by the skilled practitioner.

EXAMPLE 5. Use of Compositions Containing the Compound of the Present Invention for Treating Cancer The present invention further relates to a method of treating cancer comprising the administration of an "antitumor effective amount" of the composition of the present invention. The "antitumor effective amount" is defined, for example, as that amount required to be administered to an individual patient to achieve an antitumor effective blood and/or tissue level of the compound of the present invention to kill or inhibit the growth of the tumor; the effective blood level might be chosen, for example, as that level (e.g., $10^{-7}$–$10^{-4}$M from FIGS. 2 and 3) to kill or inhibit the growth of tumor cells in a screening assay. Alternatively, the "antitumor effective blood level" might be defined as that concentration of the compound of the present invention needed to inhibit markers of the tumor in the patient's blood, or which slows or stops the growth of the patient's tumor, or which causes the patient's tumor to regress or disappear, or which renders the patient asymptomatic to the particular tumor or which renders an improvement in the patient's subjective sense of condition. Since a fixed "antitumor effective blood level" is used as the preferred endpoint for dosing, the actual dose and schedule for drug administration for each patient may vary depending upon interindividual differences in pharmacokinetics, drug disposition and metabolism. Moreover, the dose may vary when the compound is used in combination with other drugs.

While the foregoing invention has been described in some detail for purposes of clarity and understanding, it will be appreciated by one skilled in the art from a reading of this disclosure that various changes in form and detail can be made without departing from the true scope of the invention.

We claim:

1. A new antitumor compound, in substantially pure form, having the structure:

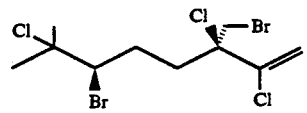

2. A pharmaceutical composition comprising the compound of claim 1 and a pharmaceutically acceptable carrier.

3. A method of treating cancer which comprises administering to a patient in need thereof, an antitumor effective amount of the compound according to claim 1.

4. The method of claim 3, wherein said cancer is leukemia, lymphoma or a solid tumor.

5. The method of claim 4, wherein said cancer is a solid tumor.

6. The method of claim 5, wherein said solid tumor is selected from the group consisting of lung cancer, colon cancer, brain cancer, melanoma, ovarian cancer, renal cancer, head and neck cancer, testicular cancer, germ-line cancers, endocrine tumors, uterine cancer, breast cancer, sarcomas, gastric cancer, hepatic cancer, esophageal cancer and pancreatic cancer.

7. The method of claim 6, wherein said solid tumor is selected from the group consisting of brain cancer, renal cancer and colon cancer.

8. The method according to claim 7, wherein said cancer is a brain cancer.

9. The method according to claim 7, wherein said cancer is a renal cancer.

10. The method according to claim 7, wherein said cancer is a colon cancer.

11. The method of claim 3, wherein the antitumor effective amount of the compound is from about $10^{-7}$ M to about $10^{-4}$ M.

12. The method of claim 4, wherein the antitumor effective amount of the compound is from about $10^{-7}$ M to about $10^{-4}$ M.

13. The method of claim 5, wherein the antitumor effective amount of the compound is from about $10^{-7}$ M to about $10^{-4}$ M.

14. The method of claim 6, wherein the antitumor effective amount of the compound is from about $10^{-7}$ M to about $10^{-4}$ M.

15. The method of claim 7, wherein the antitumor effective amount of the compound is from about $10^{-7}$ M to about $10^{-4}$ M.

16. The method of claim 8, wherein the antitumor effective amount of the compound is from about $10^{-7}$ M to about $10^{-4}$ M.

17. The method of claim 11 wherein said compound is administered orally, by inhalation, by injection, as an ointment, or as a suppository.

18. The method of claim 12 wherein said compound is administered orally, by inhalation, by injection, as an ointment, or as a suppository.

19. The method of claim 13 wherein said compound is administered orally, by inhalation, by injection, as an ointment, or as a suppository.

20. The method of claim 14 wherein said compound is administered orally, by inhalation, by injection, as an ointment, or as a suppository.

21. The method of claim 15 wherein said compound is administered orally, by inhalation, by injection, as an ointment, or as a suppository.

22. The method of claim 16 wherein said compound is administered orally, by inhalation, by injection, as an ointment, or as a suppository.

* * * * *

UNITED STATES PATENT AND TRADEMARK OFFICE
CERTIFICATE OF CORRECTION

PATENT NO.  : 5,283,383
DATED       : February 1, 1994
INVENTOR(S) : Boyd et al.

It is certified that error appears in the above-identified patent and that said Letters Patent is hereby corrected as shown below:

ON THE TITLE PAGE: Item

[73] Assignee:

"The United States of America as represented by the Department of Health and Human Services, Washington, D.C." should read -- The United States of America as represented by the Department of Health and Human Services, Washington, D.C., and Cornell Research Foundation, Inc., Ithaca, New York --.

Signed and Sealed this

Ninth Day of January, 1996

Attest:

BRUCE LEHMAN

Attesting Officer

Commissioner of Patents and Trademarks